United States Patent
Feiler et al.

(10) Patent No.: US 6,589,916 B1
(45) Date of Patent: Jul. 8, 2003

(54) METHOD AND COMPOSITION FOR TREATING AND PROMOTING THE GROWTH OF PLANTS

(75) Inventors: William Feiler, La Habra Heights, CA (US); Christopher Hoder, Lake Wales, FL (US)

(73) Assignee: Amvac Chemical Corporation, Los Angeles, CA (US)

( * ) Notice: Subject to any disclaimer, the term of this patent is extended or adjusted under 35 U.S.C. 154(b) by 0 days.

(21) Appl. No.: 09/415,455

(22) Filed: Oct. 8, 1999

(51) Int. Cl.$^7$ ............................................... A01N 47/12
(52) U.S. Cl. ........................................................ 504/300
(58) Field of Search ............................. 504/300; 562/27

(56) References Cited

U.S. PATENT DOCUMENTS 2,766,554 A * 10/1956 Dorman et al. ................. 47/58
2,792,327 A * 5/1957 Hunt ............................. 167/22
4,113,462 A * 9/1978 Wagner ............................ 71/7

* cited by examiner

*Primary Examiner*—S. Mark Clardy
(74) *Attorney, Agent, or Firm*—Pillsbury Winthrop LLP

(57) ABSTRACT

Described is a method for promoting the growth of plants in general and promoting the growth and enhancing the color of grass in particular. The method treats the plants and the soil in which they grow with a fungicidally effective amount of methylammonium methyldithiocarbamate, the fungicidally effective amount being insufficient to significantly retard the growth of the grass. In the practice of the invention, the plants are treated with an aqueous solution of methylammonium methyldithiocarbamate by dripping or spraying the solution onto the plants, by injecting the aqueous solution into the soil, or by drenching the soil with the aqueous solution. Significantly reduced amounts of methylammonium methyldithiocarbamate are employed to reduce damage to the plants.

23 Claims, No Drawings

METHOD AND COMPOSITION FOR TREATING AND PROMOTING THE GROWTH OF PLANTS

FIELD OF THE INVENTION

Embodiments of the present invention are directed to a method and composition for the fungicidal treatment of soil and plants to enhance seed germination, seedling development, and plant growth.

BACKGROUND OF THE INVENTION

Various dithiocarbamic acid derivatives have long been used in the art to treat soil before crops and other vegetation are planted in it. The majority of these are fungicides and herbicides of sufficient potency to kill virtually all the plant and animal life living in the soil to which the selected dithiocarbamic acid derivative is applied.

U.S. Pat. No. 2,835,625, for example, describes a composition of isopropoxycarbonyl dimethyldithiocarbamate and methods for using it to protect plants from fungal diseases. The potency of this product is such that it may be treated for four hours with ultraviolet light from an arc without losing any biological activity.

Further examples include U.S. Pat. No. 2,614,957. The patent describes a fungicidal composition containing about 75 to 99% by weight of sodium dimethyldithiocarbamate and about 25 to 1% by weight of the sodium salt of 2-mercaptobenzothiazole. U.S. Pat. No. 3,699,231 describes a biocidal composition used to inhibit the growth of microbes, particularly sulfate-reducing bacteria. The composition is a mixture of a metal carbamate derivative, such as zinc dimethyldithiocarbamate, and an aldehyde, such as formaldehyde. A related composition is a fungicide, described by U.S. Pat. No. 5,336,661, comprised of an aluminum ethyl phosphite and manganese-zinc ethylene bisdithiocarbamate. This fungicide is stated to be effective against crown and root rot that affect turfgrass.

A well-known dithiocarbamic acid derivative is sodium methyldithiocarbamate, known by its common name, metham sodium. Metham sodium is typically applied to soil to sterilize it before crops or vegetation are planted in the soil. When a fumigant solution of metham sodium comes into contact with soil, it is converted into volatile, highly toxic methyl isothiocyanate, which is known to be effective as a fungicide, pesticide, and herbicide. The highly toxic properties of metham sodium require that a significant amount of time elapse between its application and the planting of crops. This time ranges anywhere from about 7 to 30 days, depending on the qualities of the soil and the amount of metham sodium applied.

U.S. Pat. Nos. 4,994,487 and 5,075,332 describe a method of using metham sodium in particular amounts and under particular conditions so as to preserve its biocidal activity while at the same time causing the plants no harm. It is stated that metham sodium, when used in the amounts indicated, can be applied to soil at or about the time of planting of seeds without damaging the seeds or plants that grow from them; the growth of the plants is instead promoted.

The dithiocarbamic acid derivative of the present invention is methylammonium methyldithiocarbamate. Like metham sodium, it is highly toxic.

For example, U.S. Pat. No. 2,766,554 entitled "Method of Sterilizing Soil" describes a method of killing substantially all plant and an applying to it methylammonium methyldithiocarbamate. It is stated, for example, that methylammonium methyldithiocarbamate is an excellent eradicator of Morning Glory, a deep-rooted plant that is difficult to kill.

A more pleasant fate would befall the Morning Glory when treated in accordance with the present invention: in the present invention, methylammonium methyldithiocarbamate is employed not to kill plants but to promote their growth and enhance their appearance. The inventors have surprisingly discovered that methylammonium methyldithiocarbamate can be used in a manner in which it retains its fungicidal and nematodal activity while at the same time causing no damage to the plants to which it is applied. The inventors have further surprisingly discovered that the methylammonium methyldithiocarbamate can be used to improve the color of certain plants for which appearance is important, as it is, for example, for grass. The methylammonium methyldithiocarbamate also has the unexpected effect of increasing the vigor of such plants. Moreover, the advantageous results of the invention may be achieved in a matter of days to weeks, and not weeks to months.

SUMMARY OF THE INVENTION

It is an object of the present invention to provide for a composition and method to promote the growth of plants, particularly grass, while at the same time controlling the fungi, weeds, worms and other infestations that retard the plant's growth. For plants in which appearance is important, it is a further object of the invention to maintain biocidal control so that the plant vigor is enhanced at the same time that the plant's color is improved. It is another object of the invention to achieve these advantageous results in a relatively short period of time.

Described herein is the surprising discovery that methylammonium methyldithiocarbamate can be applied, in accordance with the invention, to live plants so as to promote their growth. In addition, the methods of the present invention may be used to enhance the color of crops for which color is important, such as grass. Moreover, the present invention permits one to attain these results while at the same time preserving the nematodal and fungicidal activity of the methylammonium methyldithiocarbamate. These results may remarkably be achieved in a matter of days to weeks. The result is that one who practices the invention can see significantly improved growth, color, and vigor in a given crop in a short period of time.

In preferred embodiments of the invention, the methylammonium methyldithiocarbamate is applied in aqueous form to live plants in a nematocidally effective amount. The aqueous solution may be applied by dripping, spraying, irrigating, injecting, or any other of the well-known means of delivering aqueous herbicides and fungicides to plants. Significantly reduced amounts of the methylammonium methyldithiocarbamate are used; the nemoticidally effective amount is thus insufficient to retard the growth of the plants or impair their color.

DETAILED DESCRIPTION OF THE INVENTION

In accordance with the present invention, soil in a field or lawn of plants is treated, either at about the time of planting of plant seed or after the plants are established, by contacting the soil or stand of plants with a effective amount of methylammonium methyldithiocarbamate, the amount being insufficient to significantly retard the growth of the plants or impair their color.

The rate of application of methylammonium methyldithiocarbamate to soil or plants in accordance with the invention is substantially less than those conventionally used to obtain nematodal and fungicidal activity. A significant advantage of the invention is therefore its ability to treat soil at the time of planting, shortly after it, or even well after the plants are already established. As used herein, "at the time of planting" includes methods of treatment in which the soil in a seed bed is treated with methylammonium methyldithiocarbamate either as the seed or vegetative material is being planted in the soil or shortly before such planting.

In presently preferred embodiments of the invention, the methylammonium methyldithiocarbamate is applied in the form of an aqueous solution. At any time during or after planting or shortly before it, the solution may be applied by dripping or spraying the solution onto the plants, by injecting the aqueous solution into the soil, by drenching the soil with the aqueous solution, or by any other of the well-known means of delivering pesticides to soil and/or plants. For example, the solution may be dripped or sprayed into a seed furrow in the seed bed as the seed or vegetative material is being planted, may be injected into the soil beneath the seed or vegetative material during planting, or the soil may be drenched by the solution shortly prior to, during, or following planting of the seed or vegetative material in the soil. Similarly, any of these or other application techniques may be used for application to an established stand of vegetative material. In this case, certain application techniques are preferred based on the manner in which the crop is being grown; for example, a plowing technique is not preferred for a grass field, but could be used for treating rows of wheat. The appropriate technique will be readily apparent to any person skilled in the agricultural and/or pesticidal arts.

In one embodiment of the invention, soil is treated in accordance with the invention at the time of planting. In other embodiments, established plants may be advantageously affected by treatment of either the soil surrounding the plants or the plants themselves. Accordingly, practice of the invention is broadly applicable to a variety of seeds, reproductive vegetative material, seedlings, and established plants. Representative, illustrative crops which may be advantageously treated at the time of seed planting include, for example, dry beans, dry peas, soy beans, sweet corn, field corn, green beans, green peas, cotton, wheat, barley, lentils, and the like. Representative, illustrative crops which may be advantageously-treated at the time of planting of reproductive vegetative material include, for example, potatoes, pineapple, flower bulbs, and the like. Representative, illustrative plants and/or seedlings which may be treated in accordance with the invention include container grown ornamentals, fruit trees, vegetable seedlings, and the like.

About 50 different types of grasses are commonly planted, any of which may be advantageously treated by the methods of the present invention. Representative grasses include the various varieties of Bermudagrass (Common, Midiron, and Ormond), Tifway II, Tifway 419, Tifdwarf, Tifgreen 328 and the hybrids thereof.

These and other grasses are commonly found in golf courses, lawn grass production sites, exercise facilities, racing turfs, parks, road shoulders, industrial development areas, housing development areas, and the like. Any of these areas are suitable for treatment by the methods of the present invention.

The precise amount of methylammonium methyldithiocarbamate to be applied to a particular plant in accordance with the invention will depend upon the sensitivities of the particular plant, the method of application, and field conditions such as the quality of the soil; all of these values, and concentration and application rates in particular, will be readily apparent to one skilled in the art. In general, the greater the rate of application, the lower the concentration of methylammonium methyldithiocarbamate needs to be. Porous soils, soils that drain well, soils that remain wet and/or cold, and soils that are high in organic content generally require a higher concentration of methylammonium methyldithiocarbamate or a higher application rate; heavy, dense soils generally require a lower application rate, as do soils that have a deep thatch layer.

The methylammonium methyldithiocarbamate is generally applied in the form of an aqueous solution at the rate of about 0.5 to 40 lbs of methylammonium methyldithiocarbamate by dry weight per treated acre for applications where the solution is applied to the soil in the seed furrow at the time of planting of the seed; at the rate of about 0.5 to 40 lbs of methylammonium methyldithiocarbamate by dry weight per treated acre of plant row for those applications where the aqueous solution is injected into the soil beneath the seed or vegetative material at the time of planting; and at the rate of about 0.5 to 40 lbs of methylammonium methyldithiocarbamate by dry weight per treated acre of soil where the solution is applied by drenching, spraying, or dripping the solution onto already established plants.

In one presently preferred embodiment of the invention, the methylammonium methyldithiocarbamate is applied in an aqueous form to an established field or lawn of grass. The aqueous solution in this embodiment is applied in an amount which is sufficient to penetrate beneath the thatch layer of the grass, but is insufficient to significantly reduce or retard the growth of the grass or impair its color. The concentration of the aqueous solution consists of about 0.25% to 25% methylammonium methyldithiocarbamate by weight, the remainder being water. The preferred application rate is about 0.5 to 20 lbs of methylammonium methyldithiocarbamate by dry weight per treated acre of soil. Methylammonium methyldithiocarbamate generally retains its fungicidal activity when applied at these rates.

In addition to the preferred concentration and application rates described above, one can effectively employ the methylammonium methyldithiocarbamate at higher concentration rate. In such applications the preferred method is to add additional water to the field to move the more concentrated solution into the root zone of the plants.

These and other embodiments of the invention may be better understood in connection with the following representative example, which is presented for purposes of illustration of the invention and not by way of limitation.

EXAMPLE 1

The effect of the application of methylammonium methyldithiocarbamate to live grass was determined in the following manner. Dilute aqueous solutions of three salts of the same dithiocarbamic acid derivative were prepared: methylammonium methyldithiocarbamate, sodium methyldithiocarbamate, and potassium methyldithiocarbamate. The solutions were prepared by mixing the dithiocarbamic acid derivative with water to achieve a concentration of between about 1.2 and 3.5% by weight.

Three plots of grass of substantially equal type, quality, color, and size were selected at each of several golf courses throughout the state of Florida. The grass at these courses consisted of one or a combination of Bermudagrass (Common, Midiron, and Ormond), Tifway II, Tifway 419, Tifdwarf, and Tifgreen 328 grasses. To each of these plots one of the methyldithiocarbamate salts were applied via an ordinary above-ground spraying system in an amount equivalent to between about 0.5 to 40 lbs of methyldithiocarbamate salt per acre of soil. All applications were watered in with ½ inch of water within 20 minutes of treatment, which moved the dithiocarbamic acid derivative into and slightly below the root zone of the grass. The plots were treated in the above-described manner once per month during the months indicated in Table 2, below.

The results of treating each plot with the methyldithiocarbamate salts were evaluated from 1 to 2 weeks after treatment by examining the appearance of the grass leaves. A score was assigned to each plot according to the following scale: 0=burning of leaf tissue; 1=bronzing of leaf tissue; 2=burning of the tip of the leaf tissue; 3=No burning or change in color of the leaf tissue; 4=good greening of the leaf tissue; 5=excellent greening of the leaf tissue. Where two values were assigned, the plot contained a substantial number of grass leaves of one score and a substantial number of the other score. Table 2 summarizes the results of the treatment described above.

TABLE 2

METHYLDITHIOCARBAMATE TRIALS

| COURSE | MONTH TREATED[1] | SODIUM | POTASSIUM | METHYL AMMONIUM | TIME OF EVALUATION |
|---|---|---|---|---|---|
| 1. Grenelefe Resort | January | 3 | 0 | 4 | 2 weeks |
|  | February | 3 | 1 | 3–4 | 2 weeks |
|  | March | 3–4 | 0–1 | 4 | 2 weeks |
| 2. Long Boat Key | February | 2 | 1 | 4 | 2 weeks |
|  | March | 3 | 1–2 | 4 | 2 weeks |
|  | April | 3 | 1–2 | 4 | 1 week |
| 3. Indian River Club | March | 3 | 1 | 4 | 2 weeks |
|  | April | 3 | 0–1 | 4 | 1 week |
|  | May | 3–4 | 1–2 | 4 | 1 week |
| 4. La Cita C.C.[2] | March | 4 | 2 | 5 | 1 week |
|  | June | 3–4 | 1 | 5 | 1 week |
|  | September | 4 | 2 | 5 | 1 week |
| 5. Wellington C.C. | April | 3 | 1 | 5 | 2 weeks |
| 6. Dodgertown C.C. | April | 3 | 0 | 4 | 1 week |
|  | May | 3–4 | 1–2 | 4 | 1 week |
| 7. Westchester C.C. | April | 3 | 1 | 4 | 1 week |
| 8. President Club | May | 4 | 0 | 5 | 1 week |
|  | July | 4 | 2–3 | 5 | 1 week |
| 9. Vero Beach C.C. | June | 3–4 | 1 | 4–5 | 1 week |
| 10. Admirals Cove | July | 3–4 | 1–2 | 4 | 1 week |
| 11. Moorings C.C. | August | 4 | 1 | 5 | 1 week |
| 12. Hawks Nest C.C. | August | 4 | 0 | 5 | 1 week |
| 13. Woodmont C.C. | June | 4 | 1–2 | 5 | 1 week |
|  | September | 4 | 2–3 | 5 | 1 week |

[1]All months are in 1998;
[2]C.C. = "Country Club"

As can be seen from Table 2, areas treated with methylammonium methyldithiocarbamate produced grass with either good or excellent greening of the leaf tissue; only one patch (Grenelefe Resort, February) contained grass in which the leaf tissue improved only marginally in color. The methylammonium methyldithiocarbamate also produced better results than the sodium methyldithiocarbamate and far better results than the potassium methyldithiocarbamate.

While embodiments of the invention have been described in connection with this illustrative example, various modifications will be apparent to those skilled in the art. Any such modifications are intended to be within the scope of the appended claims.

What is claimed is:

1. The method for treating and enhancing the growth of plants in soil, comprising treating the soil with an amount of methylammonium methyldithiocarbamate at or after the time of planting of seed or vegetative material in the soil, said amount being sufficient to promote the growth of the plants from the seed or vegetative material and to impair the growth of nematodes and fungi, but insufficient to impair the plants' color.

2. The method of claim 1, wherein the methylammonium methyldithiocarbamate is an aqueous solution.

3. The method of claim 2, wherein the aqueous solution has a concentration of about 0.25 to 50% methylammonium methyldithiocarbamate by weight.

4. The method of claim 2, wherein the aqueous solution is applied at a rate of about 0.5 to 40 lbs of methylammonium methyldithiocarbamate by dry weight per acre of soil.

5. The method of claim 2, wherein the aqueous solution is injected into the soil beneath the seed or vegetative material at or after the time of planting of the seed or vegetative material.

6. The method of claim 5, wherein the aqueous solution is injected up to about 0 to 10 cm beneath the seed or vegetative material.

7. The method of claim 2, wherein the soil is drenched with the aqueous solution.

8. The method of claim 7, wherein the soil is drenched at a rate of about 0.5 to 40 lbs of methylammonium methyldithiocarbamate by dry weight per acre of soil.

9. The method of claim 2, wherein the aqueous solution is applied by dripping or spraying the solution onto the soil.

10. The method of claim 9, wherein the aqueous solution is dripped or sprayed at a rate of about 0.5 to 20 lbs of methylammonium methyldithiocarbamate by dry weight per acre of soil.

11. The method of claim 2, wherein the aqueous solution is applied to a seed furrow in the soil at or after the time of planting of the seed or vegetative material.

12. The method of claim 11, wherein the aqueous solution is applied at a rate of about 0.5 to 20 lbs of methylammonium methyldithiocarbamate by dry weight per acre of soil.

13. A method for enhancing the growth of grass in soil, comprising treating the soil with an amount of methylammonium methyldithiocarbamate at or after the time of planting of the grass, said amount being sufficient to promote the growth of the grass and to impair the growth of nematodes and fungi, but insufficient to impair the grass's color.

14. The method of claim 13, wherein the methylammonium methyldithiocarbamate is an aqueous solution.

15. The method of claim 14, wherein the aqueous solution has a concentration of about 0.25 to 50% methylammonium methyldithiocarbamate by weight.

16. The method of claim 14, wherein the aqueous solution is applied at a rate of about 0.5 to 40 lbs of methylammonium methyldithiocarbamate by dry weight per acre of medium.

17. The method of claim 14, wherein the aqueous solution is injected into the medium.

18. The method of claim 14, wherein the medium is drenched with the aqueous solution.

19. The method of claim 14, wherein the medium is drenched at a rate of about 0.5 to 40 lbs of methylammonium methyldithiocarbamate by dry weight per acre of medium.

20. The method of claim 14, wherein the aqueous solution is applied by dripping or spraying the solution onto the medium.

21. The method of claim 14, wherein the aqueous solution is dripped or sprayed at a rate of about 0.5 to 20 lbs of methylammonium methyldithiocarbamate by dry weight per acre of soil.

22. The method of claim 14, the method further comprising:

applying the methylammonium methyldithiocarbamate in irrigation water as a drench or as a spray; and washing the grass with at least about 0.1 inch of water after the methylammonium methyldithiocarbamate application to remove substantially all of the methylammonium methyldithiocarbamate from the grass.

23. A method for treating and enhancing the growth of plants in soil, comprising treating the soil of a plant with an amount of methylammonium methyldithiocarbamate, said amount being sufficient to promote the growth of the plant and to impair the growth of nematodes and fungi, but insufficient to impair the plant's color.

* * * * *